United States Patent
Hayes, Jr. et al.

(10) Patent No.: US 9,161,840 B2
(45) Date of Patent: *Oct. 20, 2015

(54) MODULAR PROSTHETIC COMPONENT WITH IMPROVED BODY SHAPE

(75) Inventors: Daniel E. E. Hayes, Jr., Placerville, CA (US); Alfred S. Despres, III, Shingle Springs, CA (US)

(73) Assignee: Consensus Orthopedics, Inc., El Dorado Hills, CA (US)

( * ) Notice: Subject to any disclaimer, the term of this patent is extended or adjusted under 35 U.S.C. 154(b) by 445 days.

This patent is subject to a terminal disclaimer.

(21) Appl. No.: 11/036,586

(22) Filed: Jan. 14, 2005

(65) Prior Publication Data

US 2005/0283254 A1    Dec. 22, 2005

Related U.S. Application Data

(63) Continuation of application No. 09/960,175, filed on Sep. 20, 2001, now Pat. No. 6,843,806.

(60) Provisional application No. 60/233,875, filed on Sep. 20, 2000.

(51) Int. Cl.
*A61F 2/36* (2006.01)
*A61F 2/30* (2006.01)
(Continued)

(52) U.S. Cl.
CPC .............. *A61F 2/367* (2013.01); *A61F 2/30734* (2013.01); *A61F 2/36* (2013.01); *A61F 2/30771* (2013.01); *A61F 2/32* (2013.01); *A61F 2/34* (2013.01); *A61F 2/3662* (2013.01); *A61F 2002/30112* (2013.01); *A61F 2002/30156* (2013.01); *A61F 2002/30158* (2013.01); *A61F 2002/30332* (2013.01); *A61F 2002/30354* (2013.01); *A61F 2002/30405* (2013.01); *A61F 2002/30512* (2013.01); *A61F 2002/30604* (2013.01); *A61F 2002/30736* (2013.01); *A61F 2002/30738* (2013.01); *A61F 2002/30827* (2013.01); *A61F 2002/30886* (2013.01);
(Continued)

(58) Field of Classification Search
CPC ................................................ A61F 2002/3674
USPC .......... 623/20.15, 23.18, 23.35, 22.41–22.46, 623/23.44–23.46
See application file for complete search history.

(56) References Cited

U.S. PATENT DOCUMENTS 4,064,567 A * 12/1977 Burstein et al. ............ 623/23.46
4,404,693 A    9/1983 Zweymuller
(Continued)

FOREIGN PATENT DOCUMENTS

EP    0634154    1/1995
EP    0677281    10/1995
(Continued)

*Primary Examiner* — David H Willse
(74) *Attorney, Agent, or Firm* — Pandiscio & Pandiscio

(57) ABSTRACT

An improved body element for use in a modular prosthetic stem component of the sort comprising a body element and at least one other element, wherein the body element and the at least one other element are joined together by at least one modular connection, wherein the improved body element comprises an anterior wall and a posterior wall, at least one of the anterior wall and the posterior wall converging toward the other on the medial side of the body element and diverging away from the other on the lateral side of the body element, whereby the body element approximates a general wedge shape.

1 Claim, 7 Drawing Sheets

(51) Int. Cl.
    *A61F 2/32*          (2006.01)
    *A61F 2/34*          (2006.01)

(52) U.S. Cl.
    CPC ... *A61F2002/365* (2013.01); *A61F 2002/3611* (2013.01); *A61F 2002/3625* (2013.01); *A61F 2002/3652* (2013.01); *A61F 2002/3674* (2013.01); *A61F 2002/3694* (2013.01); *A61F 2220/0025* (2013.01); *A61F 2220/0033* (2013.01); *A61F 2230/0004* (2013.01); *A61F 2230/0023* (2013.01); *A61F 2230/0026* (2013.01)

(56) References Cited

U.S. PATENT DOCUMENTS

| | | | |
|---|---|---|---|
| 4,608,055 A * | 8/1986 | Morrey et al. | 623/22.46 |
| 4,778,475 A | 10/1988 | Ranawat et al. | |
| 4,790,852 A | 12/1988 | Noiles | |
| 4,813,963 A * | 3/1989 | Hori et al. | 623/23.35 |
| 4,846,839 A | 7/1989 | Noiles | |
| 5,002,578 A | 3/1991 | Luman | |
| 5,080,685 A | 1/1992 | Bolesky et al. | |
| 5,163,961 A | 11/1992 | Harwin | |
| 5,549,706 A | 8/1996 | McCarthy | |
| 5,725,592 A | 3/1998 | White et al. | |
| 5,725,594 A | 3/1998 | McTighe et al. | |
| 5,906,644 A | 5/1999 | Powell | |
| 6,187,050 B1 | 2/2001 | Khalili et al. | |
| 6,299,648 B1 * | 10/2001 | Doubler et al. | 623/23.18 |
| 6,368,353 B1 | 4/2002 | Arcand | |
| 6,428,578 B2 | 8/2002 | White | |

FOREIGN PATENT DOCUMENTS

| | | | |
|---|---|---|---|
| EP | 0709071 | 5/1996 | |
| EP | 0 611 225 | 9/1997 | |
| EP | 1004283 | 5/2000 | |
| FR | 2 651 118 | 3/1991 | |
| RU | 2 108 071 C1 * | 4/1998 | A61F 2/32 |
| WO | WO 99/47081 | 9/1999 | |

* cited by examiner

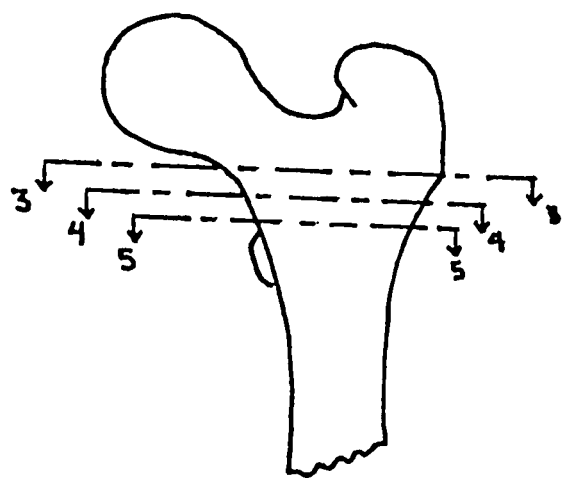
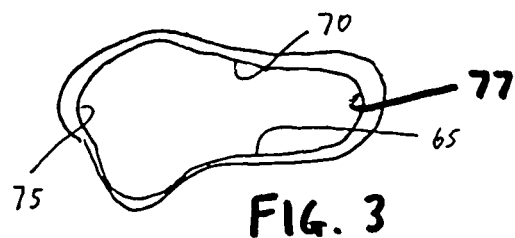
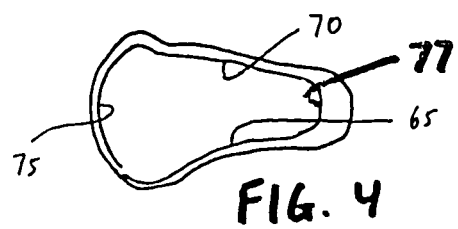
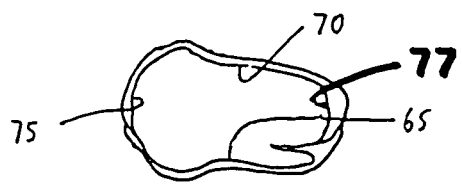
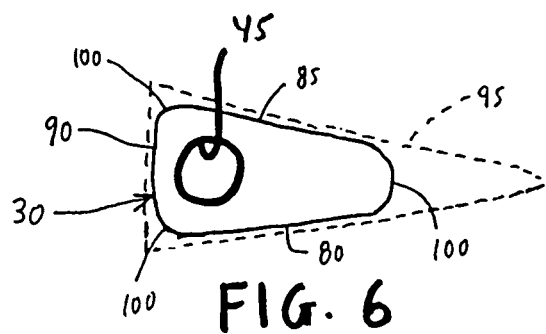

MODULAR PROSTHETIC COMPONENT WITH IMPROVED BODY SHAPE

REFERENCE TO PENDING PRIOR PATENT APPLICATION

This is a continuation of pending prior U.S. patent application Ser. No. 09/960,175, filed Sep. 20, 2001 by Daniel E. E. Hayes, Jr. et al. for MODULAR PROSTHETIC COMPONENT WITH IMPROVED BODY SHAPE, now U.S. Pat. No. 6,843,806, issued Jan. 18, 2005, which in turn claims benefit of prior U.S. Provisional Patent Application Ser. No. 60/233,875, filed Sep. 20, 2000 by Daniel E. E. Hayes, Jr. et al. for MODULAR PROSTHETIC IMPLANT. The above-identified patent and patent application are hereby incorporated herein by reference.

FIELD OF THE INVENTION

This invention relates to surgical apparatus and procedures in general, and more particularly to orthopedic prostheses for restoring a joint.

BACKGROUND OF THE INVENTION

Joint replacement surgery seeks to replace portions of a joint with prosthetic components so as to provide long-lasting function and pain-free mobility.

For example, in the case of a prosthetic total hip joint, the head of the femur is replaced with a prosthetic femoral stem component, and the socket of the acetabulum is replaced by a prosthetic acetabular cup component, whereby to provide a prosthetic total hip joint.

In the case of a prosthetic total knee joint, the top of the tibia is replaced by a prosthetic tibial component, and the bottom of the femur is replaced by a prosthetic femoral component, whereby to provide a prosthetic total knee joint.

Still other prosthetic total joints, and their constituent components, are well known in the art.

The present invention is directed to orthopedic prostheses for restoring the hip joint and, more particularly, to improved prosthetic femoral stem components.

Prosthetic femoral stem components typically comprise a proximal section for seating in the proximal section of the resected femur and presenting a ball for seating in the acetabular socket, and a distal section for seating in the femur's medullary canal so as to extend along the shaft of the femur.

It is, of course, important that the prosthetic femoral stem component make a proper fit with the surrounding bone. To this end, prosthetic femoral stem components are typically offered in a range of different sizes in an effort to accommodate variations in patient anatomy. However, despite this, it has been found that it can be difficult to provide the correct prosthetic femoral stem component for patients. This is due to the wide variation in patient anatomies and the practical limitations of hospital inventory. By way of example, where a femoral component is selected having a proximal section appropriately sized for the proximal section of the resected femur, the distal section of the prosthesis may not be appropriately sized for proper seating in the distal section of the femur. This can present serious problems for the patient, including problems relating to joint stability and pain.

On account of the foregoing, there has been substantial interest in forming prosthetic femoral stem components out of a plurality of separate elements, wherein each of the elements may be independently selected so as to most closely approximate patient anatomy, and wherein the separate elements may be assembled to one another in the operating room, using modular connections, so as to provide the best possible prosthetic femoral stem component for the patient.

Modular prosthetic femoral stem components are offered in a variety of configurations.

By way of example, a so-called "two part" modular prosthetic femoral stem component may comprise a body element and a combined neck-and-stem element. More specifically, the body element includes a central aperture through which the combined neck-and-stem element extends. The body element is selected so that its outer surface is appropriately sized for proper seating in the proximal section of a resected femur. The combined neck-and-stem element is selected so that when it is mounted to the body element and deployed within the femur, a ball located at the proximal end of the combined neck-and-stem element will be properly seated in the hip joint's corresponding acetabular cup while the distal end of the combined neck-and-stem element will be properly seated within the medullary canal of the femur. The body element and the combined neck-and-stem element are adapted to be secured to one another in the operating room, using modular connections, so as to form the complete modular prosthetic femoral stem component. Such modular connections are well known in the art.

Other types of "two part" modular prosthetic femoral stem components are also well known in the art.

By way of further example, a so-called "three part" modular prosthetic femoral stem component may comprise a body element, a neck element and a stem element. More specifically, the body element includes a central aperture into which portions of the neck element and the stem element extend. The body element is selected so that its outer surface is appropriately sized for proper seating in the proximal section of a resected femur. The neck element is selected so that when it is mounted to the remainder of the modular prosthetic femoral stem component and deployed within the femur, a ball located at the proximal end of the neck element will be properly seated in the hip joint's corresponding acetabular cup. The stem element is selected so that its outer surface is appropriately sized for proper seating within the medullary canal of the femur. The body element, the neck element and the stem element are adapted to be secured to one another in the operating room, using modular connections, so as to form the complete modular prosthetic femoral stem component. Again, such modular connections are well known in the art.

Other types of "three part" modular prosthetic femoral stem components are also well known in the art.

Thus it will be seen that the modular prosthetic femoral stem component generally comprises: (1) a motion structure that reproduces the motion of the original, natural joint; and (2) a load structure that transmits the loads caused by that motion (e.g., walking) to the remaining bone of the resected femur. The motion structure generally comprises the neck (and ball) portion of the modular prosthetic femoral stem component. The load structure generally comprises two portions: a body portion for the transmission of axial and torsional loads to the remaining bone of the resected femur, and a stem portion to assist the body portion in resisting bending loads placed upon the body portion. In this context, the body portion is the aforementioned body element of the aforementioned "two part" modular prosthetic femoral stem component and the aforementioned body element of the aforementioned "three part" modular prosthetic femoral stem component.

The goal of the body element of a modular prosthetic femoral stem component is to transmit loads to the remaining bone of the resected femur in the same regions that the bone originally carried those loads. At the ends of the bone, this is indicated by the areas of greatest cortical bone thickness or cancellous bone density. Bone grows in response to mechanical stress. Where bone is needed to resist load, it forms; where it is not needed to resist load, it is resorbed. This principle is known as Wolff's Law. The loads generated by joint motion are preferentially carried by the bone at the end nearest the joint. If a prosthesis bypasses this region in favor of loading the more central section of the bone, resorption at the end of the bone will result. This can eventually lead to fracture of the bone or loosening of the prosthesis.

Thus, in order to transfer loads to the correct region of the bone, and to transfer the loads uniformly in that region, the body element of the prosthesis should, ideally, closely but not exactly approximate the inner contour of the hard cortical bone. More particularly, it has been found that it is preferable to leave a small amount of compacted cancellous bone between the body element of the prosthesis and the cortical bone. This is because the cancellous bone is significantly more metabolically active than the cortical bone and, as such, able to more quickly establish bone ingrowth with the prosthesis and remodel so as to carry the load. The body element should also fill the inner canal of the bone to a large extent so as to help resist torsional loads placed upon it.

SUMMARY OF THE INVENTION

Accordingly, one object of the present invention is to provide an improved configuration for the body element of a modular prosthetic femoral stem component.

Another object of the present invention is to provide an improved modular prosthetic femoral stem component.

And another object of the present invention is to provide an improved prosthetic total hip joint.

Still another object of the present invention is to provide an improved method for restoring a hip joint.

These and other objects are addressed by the provision and use of the present invention.

In one form of the invention, there is provided an improved body element for use in a modular prosthetic stem component of the sort comprising a body element and at least one other element, wherein the body element and the at least one other element are joined together by at least one modular connection, wherein the improved body element comprises an anterior wall and a posterior wall, at least one of the anterior wall and the posterior wall converging toward the other on the medial side of the body element and diverging away from the other on the lateral side of the body element, whereby the body element approximates a general wedge shape.

In another form of the invention, there is provided an improved modular prosthetic stem component comprising a body element and at least one other element, wherein the body element and the at least one other element are joined together by at least one modular connection; and further wherein the body element comprises an anterior wall and a posterior wall, at least one of the anterior wall and the posterior wall converging toward the other on the medial side of the body element and diverging away from the other on the lateral side of the body element, whereby the body element approximates a general wedge shape.

In another form of the invention, there is provided an improved prosthetic total hip joint comprising a modular prosthetic stem component and a prosthetic acetabular cup component, wherein the modular prosthetic stem component comprises a body element and at least one other element, wherein the body element and the at least one other element are joined together by at least one modular connection; and further wherein the body element comprises an anterior wall and a posterior wall, at least one of the anterior wall and the posterior wall converging toward the other on the medial side of the body element and diverging away from the other on the lateral side of the body element, whereby the body element approximates a general wedge shape.

In another form of the invention, there is provided an improved method for restoring a hip joint, the method comprising providing an improved prosthetic total hip joint comprising a modular prosthetic stem component and a prosthetic acetabular cup component, wherein the modular prosthetic stem component comprises a body element and at least one other element, wherein the body element and the at least one other element are joined together by at least one modular connection; and further wherein the body element comprises an anterior wall and a posterior wall, at least one of the anterior wall and the posterior wall converging toward the other on the medial side of the body element and diverging away from the other on the lateral side of the body element, whereby the body element approximates a general wedge shape; and deploying the improved prosthetic total hip joint in the patient.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein like numbers refer to like parts and further wherein:

FIG. 2 is a schematic view of the proximal end of a femur prior to resection;

FIG. 3 is a schematic sectional view taken along line 3-3 of FIG. 2;

FIG. 4 is a schematic sectional view taken along line 4-4 of FIG. 2;

FIG. 5 is a schematic sectional view taken along line 5-5 of FIG. 2;

FIG. 6 is a schematic top plan view of a body element formed in accordance with the present invention;

DETAILED DESCRIPTION OF THE PREFERRED EMBODIMENTS

Figure 1:
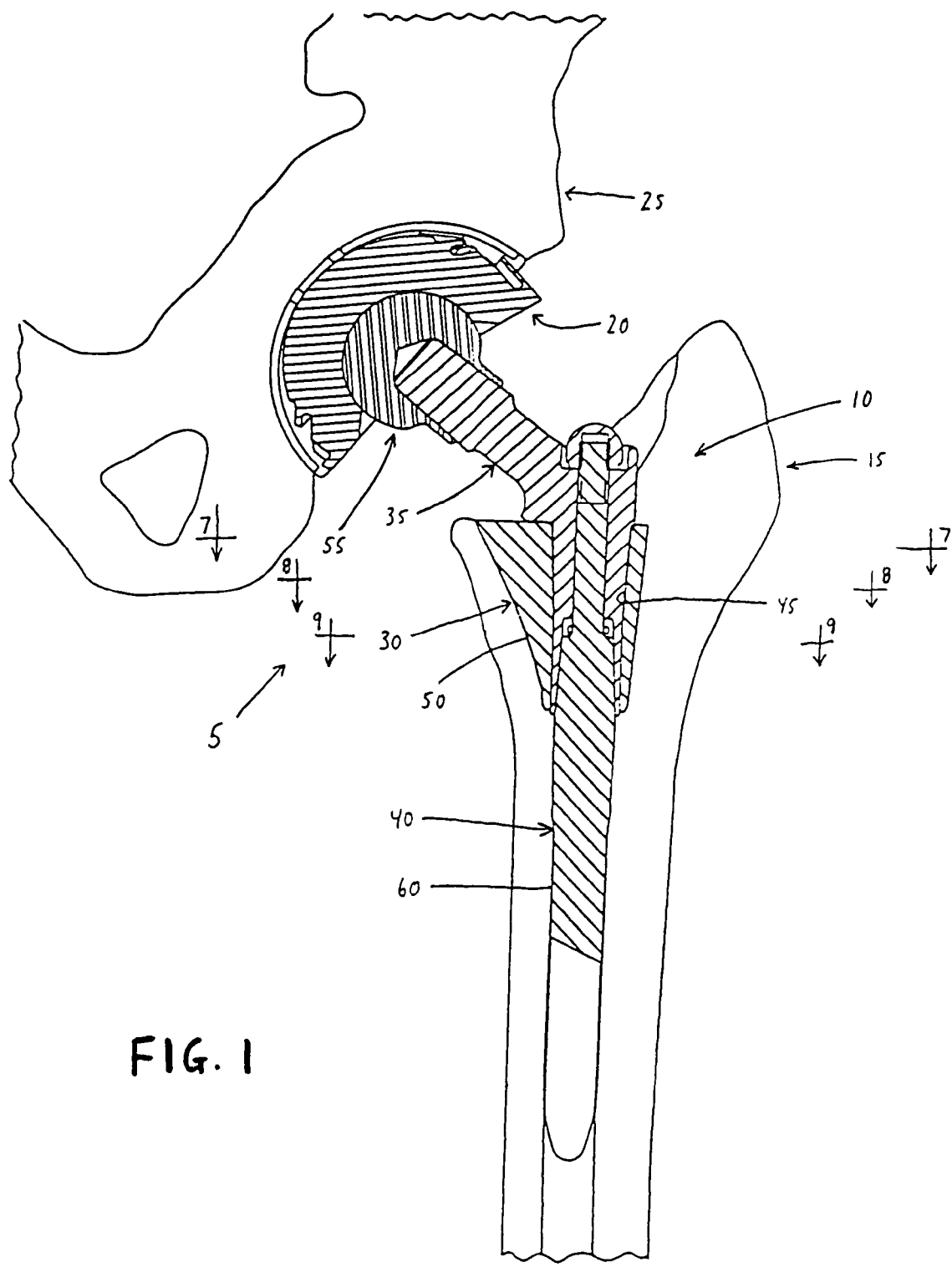
FIG. 1 is a schematic side view of a prosthetic total hip joint using a modular prosthetic femoral stem component formed in accordance with the present invention.

Looking first at FIG. 1, there is shown a prosthetic total hip joint 5 formed in accordance with the present invention. Prosthetic total hip joint 5 generally comprises a modular prosthetic femoral stem component 10 for seating in the proximal section of a resected femur 15, and a prosthetic acetabular cup component 20 for seating in the socket of the acetabulum 25.

Modular prosthetic femoral stem component 10 is formed in accordance with the present invention. Modular prosthetic femoral stem component 10 generally comprises a body element 30, a neck element 35 and a stem element 40. Body element 30 includes a central aperture 45 into which portions of neck element 35 and stem element 40 extend. As will hereinafter be discussed in further detail, body element 30 is configured and selected so that its outer surface 50 is appropriately sized for proper seating in the proximal section of resected femur 15. Neck element 35 is selected so that when it is mounted to the remainder of modular prosthetic femoral stem component 10 and deployed within femur 15, the neck element's ball 55 will be properly seated in the hip joint's corresponding acetabular cup 20. Stem element 40 is selected so that its outer surface 60 is appropriately sized for proper seating within the medullary canal of femur 15.

Body element 30, neck element 35 and stem element 40 are adapted to be secured to one another using a modular connection so as to form the complete prosthetic femoral stem component 10. Such modular connections are well known in the art.

In accordance with the present invention, body element 30 is configured so as to transmit loads to the resected femur 15. To that end, body element 30 has a profile which approximates, but is preferably undersized relative to, the profile of the resected femur's cortical bone.

More particularly, and looking next at FIG. 2, there is shown the proximal end of a natural femur. As seen in FIGS. 3-5, the profile of the femur's cortical bone changes along the femur's length. It can be seen that the femur's anterior wall 70 is located at an angle with respect to the femur's posterior wall 65, and that the femur's lateral aspect 75 and medial aspect 77 complete this general wedge shape.

Body element 30 is configured so that it closely approximates this general wedge shape. This is achieved by providing a body element which has an anterior wall and posterior wall, and wherein at least one of the anterior wall and posterior wall converges towards the other on the medial side of the body element and diverges away from the other on the lateral side of the body element.

Looking next at FIG. 6, in one preferred form of the invention, body element 30 has an anterior wall 85, a posterior wall 80 and a lateral aspect 90 which together form a generally triangular configuration 95 (FIG. 6), except that each of the vertices 100 preferably has a rounded configuration. In one preferred form of the invention, the generally triangular configuration 95 preferably comprises an isosceles triangle, although it may also comprise any other sort of triangle, e.g., a right triangle, an "irregular" triangle (i.e., a triangle with three different vertex angles) or an equilateral triangle.

This general profile may contain cutouts, slots, grooves or the like as long as the profile generally creates a shape which has three substantially flat sides, none of which are parallel to the others. Portions of the body may have the same or different triangular shape as vertically adjacent sections of the body, as need dictates.

Figure 7:
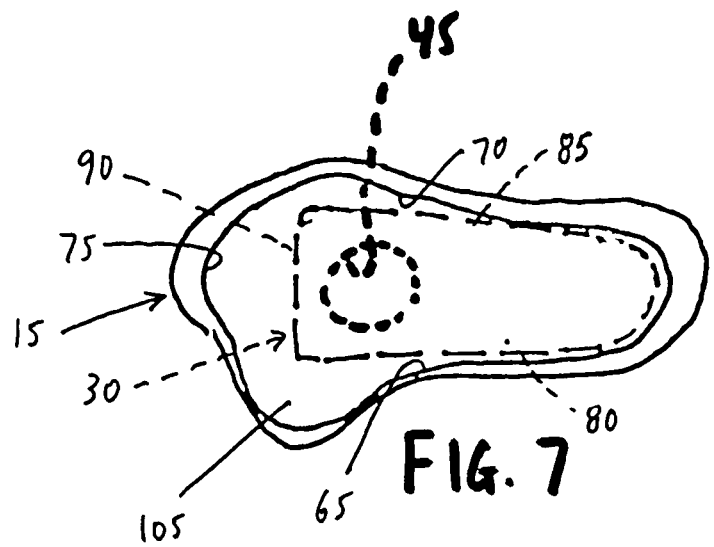
FIG. 7 is a schematic sectional view taken along line 7-7 of FIG. 1.
Figure 8:
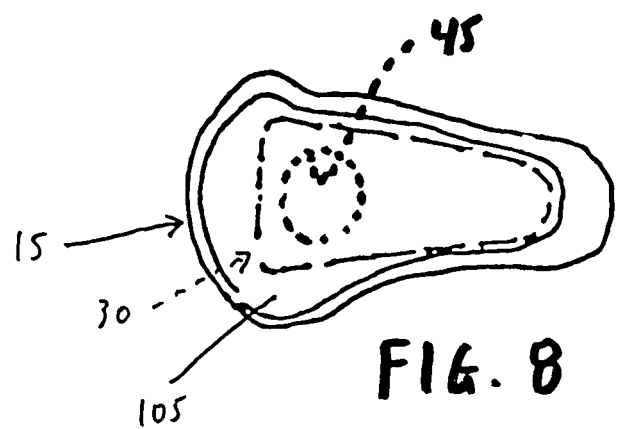
FIG. 8 is a schematic sectional view taken along line 8-8 of FIG. 1.
Figure 9:
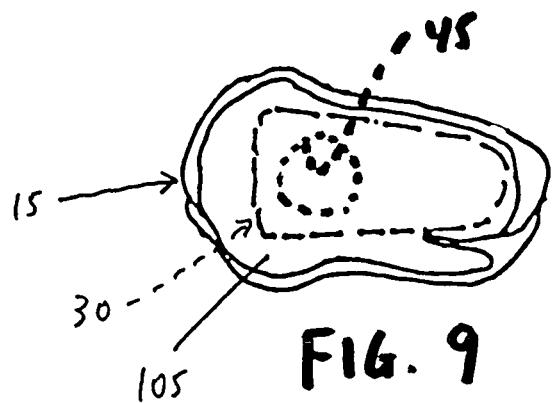
FIG. 9 is a schematic sectional view taken along line 9-9 of FIG. 1.

As noted above, body element 30 is configured so that it closely approximates the general wedge shape of the femur's cortical bone. Preferably, however, body element 30 is slightly undersized relative to the perimeter of the femur's cortical bone, such as is shown in FIGS. 7-9. This construction permits a small amount of compacted cancellous bone 105 to be left between body element 30 and the femur's cortical bone. As noted above, the presence of this metabolically active cancellous bone facilitates bone ingrowth and bone remodeling.

It is also possible to form body element 30 with other configurations so that it closely approximates the general wedge shape of the femur's cortical bone.

By way of example, it is possible to form the body element for a modular prosthetic femoral stem component with a generally trapezoidal configuration.

Figure 10:
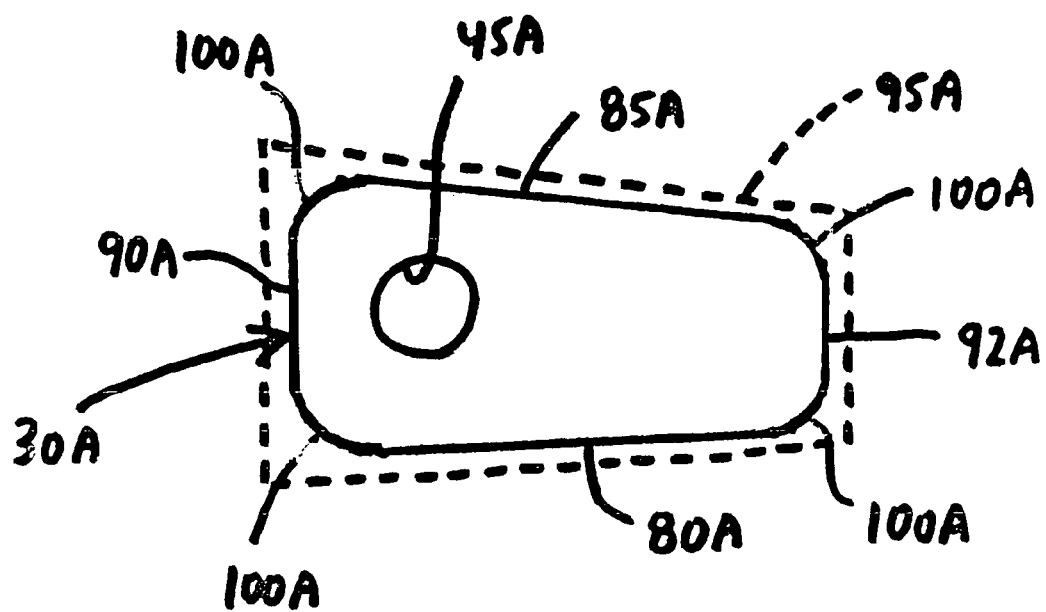
FIG. 10 is a schematic top plan view of an alternative form of body element also formed in accordance with the present invention.

More particularly, and looking now at FIG. 10, body element 30A has an anterior wall 85A, a posterior wall 80A, a lateral aspect 90A and a medial aspect 92A which together form a generally trapezoidal configuration 95A, except that each of the vertices 100A preferably has a rounded configuration.

This general profile may contain cutouts, slots, grooves or the like as long as the profile generally creates a shape which has four substantially flat sides, only two of which (i.e., the lateral aspect and the medial aspect) are parallel to one another. Portions of the body may have the same or different trapezoidal shape as vertically adjacent sections of the body, as need dictates.

Figure 11:
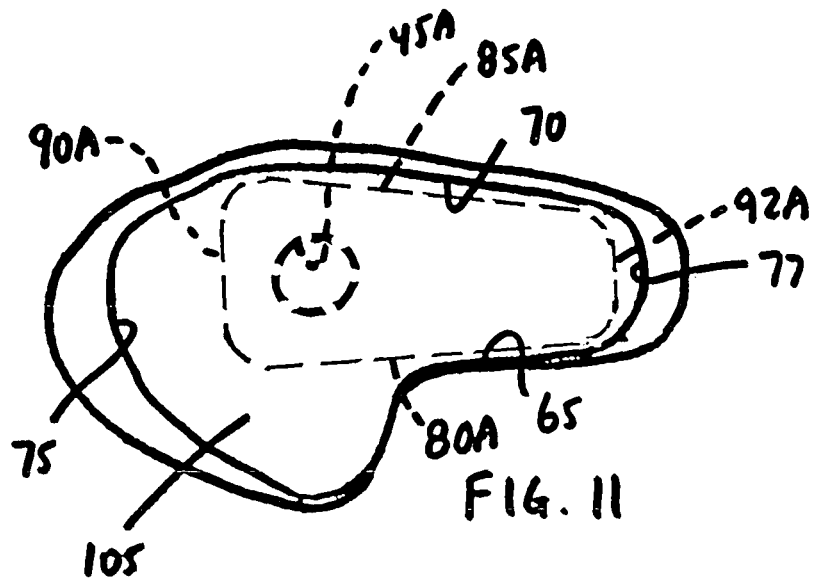
FIG. 11 is a schematic sectional view like that of FIG. 7, except incorporating the alternative form of body element shown in FIG. 10.
Figure 12:
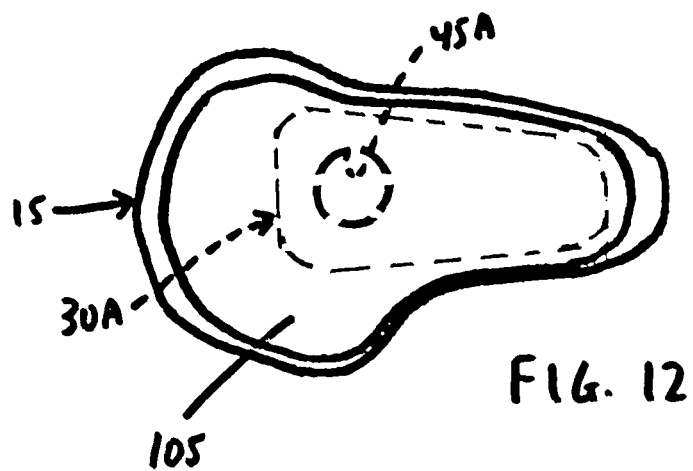
FIG. 12 is a schematic sectional view like that of FIG. 8, except incorporating the alternative form of body element shown in FIG. 10.
Figure 13:
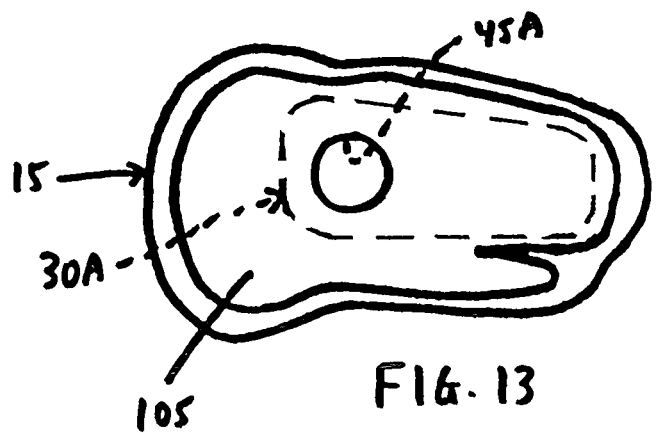
FIG. 13 is a schematic sectional view like that of FIG. 9, except incorporating the alternative form of body element shown in FIG. 10.

As noted above, body element 30A is configured so that it closely approximates the general wedge shape of the tibia's cortical bone. Preferably, however, body element 30A is slightly undersized relative to the perimeter of the femur's cortical bone, such as is shown in FIGS. 11-13. This construction permits a small amount of compacted cancellous bone 105 to be left between body element 30A and the femur's cortical bone. As noted above, the presence of this metabolically active cancellous bone facilitates bone ingrowth and bone remodeling.

Figure 14:
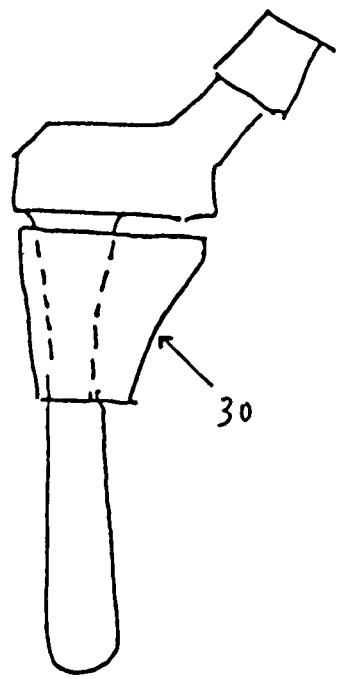
FIGS. 14-16 are schematic views of alternative forms of modular prosthetic femoral components utilizing the present invention.
Figure 16:
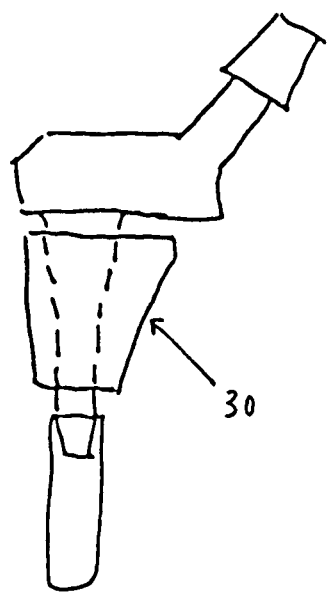
Figure 15:
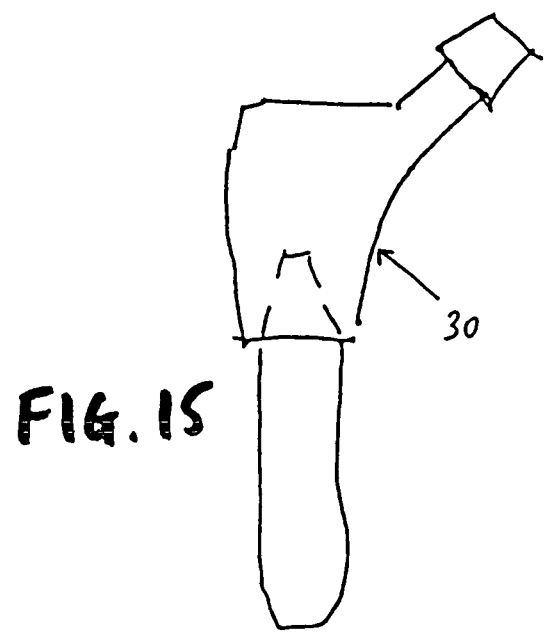

In FIGS. 1-13, the improved configuration for the body element is discussed in the context of a so-called "three part" modular prosthetic femoral stem component. However, it should be appreciated that the improved configuration for the body element can also be employed with other types of modular prosthetic femoral stem components, e.g., a so-called "two part" modular prosthetic femoral stem component such as is shown in FIG. 14 or FIG. 15; other types of "three part" modular prosthetic femoral stem components of the sort well known in the art; a so-called "four part" modular prosthetic femoral stem component such as is shown in FIG. 16; or other types of modular prosthetic femoral stem components of the sort well known in the art.

It should, of course, be appreciated that various modifications may be made to the preferred embodiments disclosed herein without departing from the scope of the present invention.

What is claimed is:

1. A prosthetic total hip joint comprising:
    a modular prosthetic femoral stem component for seating in a proximal section of a resected femur; and
    a prosthetic acetabular cup component for seating in a socket of an acetabulum;
    wherein said modular prosthetic femoral stem component comprises a body element, a neck element, and a stem element;
    wherein said body element consists of four substantially flat sides comprising an anterior wall, a posterior wall, a lateral aspect, and a medial aspect, which are configured so as to form a generally trapezoidal configuration comprising four vertices, with said lateral aspect and said medial aspect being generally parallel to one another, and with the anterior wall and the posterior wall tapering towards one another in the medial direction, so as to provide rotational stability within the resected femur; and wherein each of the four vertices of said body element is provided with a rounded non-angular configuration;

said body element being sized and configured to closely approximate the inner contour of the hard cortical bone of the resected femur while leaving a small amount of compacted cancellous bone between the body element and the cortical bone of the resected femur, such that said body element is adapted to fit in the resected femur;

said body element being provided with an aperture into which a portion of said neck element and said stem element extend;

wherein said body element and said stem element are joined together by a modular connection;

said stem element being of a size and configuration for seating within a medullary canal of the femur;

wherein said body element and said neck element are joined together by a second modular connection;

wherein said neck element is provided with a ball portion fixed thereon and adapted for seating in said acetabular cup;

said body element, said neck element, and said stem element being adapted to be secured to one another to form said prosthetic femoral stem component.

* * * * *